(12) United States Patent
Cahan et al.

(10) Patent No.: US 10,960,092 B2
(45) Date of Patent: Mar. 30, 2021

(54) AUTOMATIC ERADICATION OF BIO-RELATED CONTAMINANTS FROM HANDLES

(71) Applicant: International Business Machines Corporation, Armonk, NY (US)

(72) Inventors: Amos Cahan, Dobbs Ferry, NY (US); Guy M. Cohen, Ossining, NY (US); Lior Horesh, North Salem, NY (US); Raya Horesh, North Salem, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/228,303

(22) Filed: Dec. 20, 2018

(65) Prior Publication Data

US 2019/0117806 A1 Apr. 25, 2019

Related U.S. Application Data

(62) Division of application No. 15/157,922, filed on May 18, 2016, now Pat. No. 10,183,084.

(51) Int. Cl.
*A61L 2/10* (2006.01)
*A61L 2/26* (2006.01)
*A61L 2/24* (2006.01)

(52) U.S. Cl.
CPC ...... *A61L 2/10* (2013.01); *A61L 2/24* (2013.01); *A61L 2/26* (2013.01); *A61L 2202/14* (2013.01); *A61L 2202/17* (2013.01)

(58) Field of Classification Search
CPC ... A61L 2/08; A61L 2/084; A61L 2/10; A61L 2/24; A61L 2/26; A61L 2202/12; A61L 2202/121; A61L 2202/14; A61L 2202/15
See application file for complete search history.

(56) References Cited

U.S. PATENT DOCUMENTS

| | | |
|---|---|---|
| 7,175,807 B1 | 2/2007 | Jones |
| 7,989,779 B1 | 8/2011 | Ray et al. |

(Continued)

FOREIGN PATENT DOCUMENTS

WO WO2013025894 A2 2/2013

OTHER PUBLICATIONS

List of IBM Patents or Applications Treated as Related (2 pages).

*Primary Examiner* — Timothy C Cleveland
(74) *Attorney, Agent, or Firm* — Kristofer Haggerty; Michael J. Chang, LLC (57) ABSTRACT

Techniques for automatically eradicating microorganisms (e.g., germs, bacteria, and/or viruses) from appliance handles using ultraviolet (UV) light are provided. In one aspect, a system for eradicating biological contaminants from a handle on an appliance door is provided. The system includes a UV light emitter for producing UV disinfecting light during a cleaning cycle; and a waveguide coating on the handle, coupled to the UV light emitter, for propagating the UV disinfecting light over a surface of the handle. The system can also include a control module for controlling the UV light emitter; and at least one sensor for providing data to the control module as to when to initiate or halt a cleaning cycle. A method for eradicating biological contaminants from a handle on an appliance door using the present system is also provided.

18 Claims, 6 Drawing Sheets

(56) References Cited

U.S. PATENT DOCUMENTS

| | | |
|---|---|---|
| 8,114,346 B2 | 2/2012 | Hyde et al. |
| 8,993,988 B2 | 3/2015 | Nathan et al. |
| 2009/0117001 A1 | 5/2009 | Hyde et al. |
| 2010/0140499 A1 | 6/2010 | Casale |
| 2011/0174992 A1 | 7/2011 | Sakita |
| 2011/0291995 A1 | 12/2011 | Shr et al. |
| 2012/0176241 A1 | 7/2012 | Pasch et al. |
| 2013/0045132 A1 | 2/2013 | Tumanov |
| 2014/0048724 A1 | 2/2014 | Marshall |
| 2014/0208541 A1 | 7/2014 | Cowburn |
| 2016/0070404 A1 | 3/2016 | Kerr et al. |
| 2016/0114067 A1* | 4/2016 | Dobrinsky ............ A61L 2/10 250/461.1 |

* cited by examiner

AUTOMATIC ERADICATION OF BIO-RELATED CONTAMINANTS FROM HANDLES

CROSS-REFERENCE TO RELATED APPLICATION(S)

This application is a divisional of U.S. application Ser. No. 15/157,922 filed on May 18, 2016, now U.S. Pat. No. 10,183,084, the disclosure of which is incorporated by reference herein.

FIELD OF THE INVENTION

The present invention relates to removing bio-related contaminants from appliances, and more particularly, to techniques for automatically eradicating bio-contaminants such as microorganisms (e.g., germs, bacteria, and/or viruses), nucleic acids (DNA and RNA), proteins such as enzymes (e.g., RNase), and other potentially harmful bio-materials from appliance handles using ultraviolet (UV) light.

BACKGROUND OF THE INVENTION

Handles on appliances, e.g., refrigerators and microwaves in a home, laboratory equipment, etc. are among the most contaminated (with germs, bacteria, and/or viruses) elements one encounters on a daily basis. Namely, due to frequent contact of appliance user's hands with food (such as raw ingredients) and again with the appliance's handle, and due to the multiplicity of appliance users (either in residential settings, office settings and/or commercial use as in restaurants or in laboratories) handles become hubs of germs. According to the Centers for Disease Control (CDC), food-borne diseases cause about 76 million illnesses, 325,000 hospitalizations, and 5,000 deaths in the United States each year. A variety of different disease causing microorganisms, such as *Escherichia coli* and *Staphylococcus aureus*, can be transmitted by dirty hands. Some other settings where bio-contaminates are a concern include: contamination of tests involving nucleic acid amplification, where foreign nucleic acids can contaminate specimens, or where RNases may alter tested nucleic acids; and hospital settings, where pathogenic microorganisms, especially multi-drug resistant bacteria, as well as spores, may be transferred from one patient to another through the environment, with contact of patients or medical personnel with handles being an important way of transmission.

Disinfecting wipes are effective in eliminating some types of microorganisms. However, these are too cumbersome for regular use, and can pose environmental concerns. Users can wear gloves to reduce the spread of germs. However, if the gloves themselves come in contact with contaminates or germs, their efficacy becomes negligible. Regular use of gloves is also cumbersome, and impractical in certain setting such as in a household. Other measures have been proposed, such as the use of pedals or other foot activated means to operate appliances. Yet, closure of the door, cover, or lid is still performed using the handle, and the pedal is not amendable for all appliances.

Thus, there is a need for an effective mechanism to eradicate bio-related contamination from the surface of appliance door handles.

SUMMARY OF THE INVENTION

The present invention provides techniques for automatically eradicating bio-contaminants from appliance handles using ultraviolet (UV) light. In one aspect of the invention, a system for eradicating biological contaminants from a handle on an appliance door is provided. The system includes a UV light emitter for producing UV disinfecting light during a cleaning cycle; and a waveguide coating on the handle, coupled to the UV light emitter, for propagating the UV disinfecting light over a surface of the handle. The system can also include a control module for controlling the UV light emitter; and at least one sensor for providing data to the control module as to when to initiate or halt a cleaning cycle.

In another aspect of the invention, a method for eradicating biological contaminants from a handle on an appliance door is provided. The method includes the steps of: monitoring a state of the appliance door as either opened or closed; and initiating a cleaning cycle when the appliance door is closed by producing UV disinfecting light and propagating the UV disinfecting light over a surface of the handle using a waveguide coating on the handle. The cleaning cycle can be halted whenever a user approaches the handle.

A more complete understanding of the present invention, as well as further features and advantages of the present invention, will be obtained by reference to the following detailed description and drawings.

DETAILED DESCRIPTION OF PREFERRED EMBODIMENTS

Figure 1:
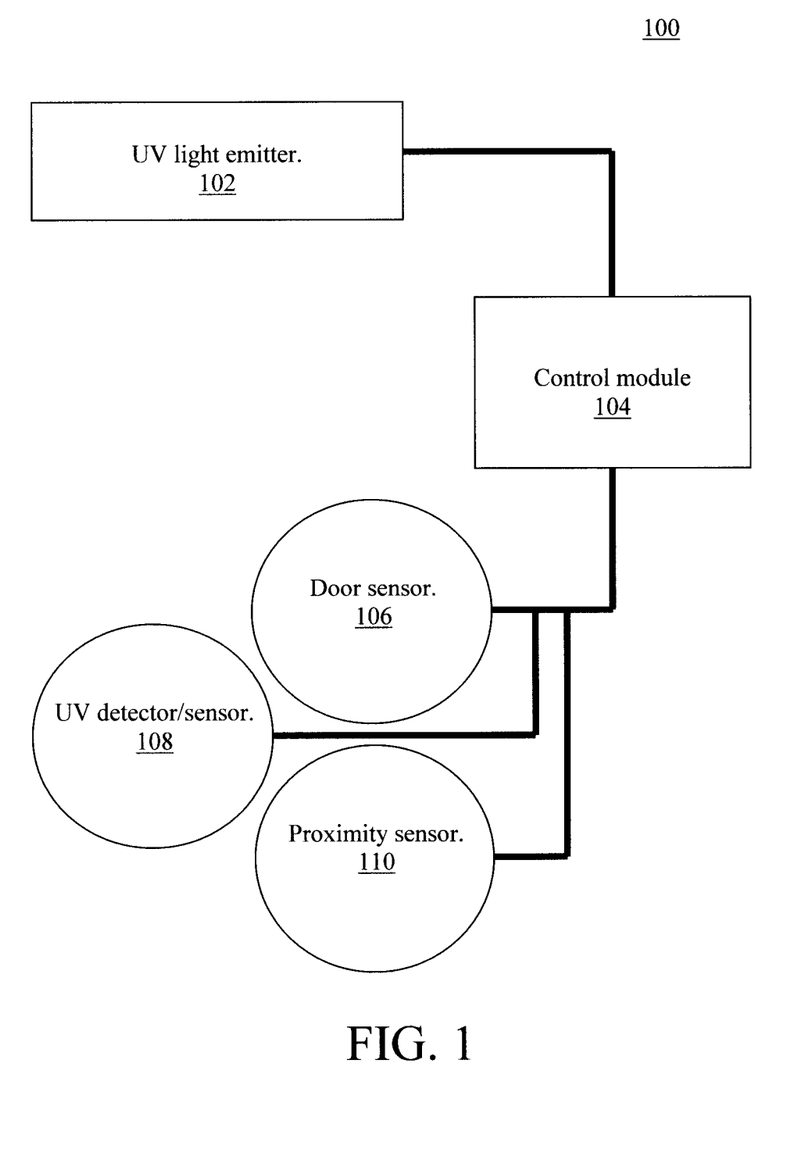
FIG. 1 is a diagram illustrating an exemplary system for automatically eradicating bio-related contaminants from appliance handles according to an embodiment of the present invention.

Provided herein are techniques to eradicate bio-related contamination (such as microorganisms (e.g., germs, bacteria, and/or viruses), nucleic acids (DNA and RNA), proteins such as enzymes (e.g., RNase), and other potentially harmful bio-materials) from the surface of appliance door handles using ultraviolet (UV) light. See, for example, FIG. 1 which provides an overview of the present system 100 for automatically eradicating bio-related contaminants from appliance handles. According to an exemplary embodiment, system 100 is contained within the appliance itself. Thus, a notable advantage is that it enables use of the appliance's power feed. Therefore, the availability of power to run the system is not an issue. The application of the present techniques to appliance handles is merely one example. The techniques described herein can be used in a variety of different settings for eradicating bio-contaminants, such as hospital bedsides, laboratory fume hood surfaces, incubators (for microorganisms/cells) or other surfaces (e.g., for preparing food, handling biological samples, preparing medications, mats, etc.). The access to a constant power source (as is the case for an appliance) is, in these other settings as well, also an advantage. As shown in FIG. 1, system 100 includes a UV light emitter 102 under the control of a control module 104, and a variety of sensors 106, 108, 110, etc. that provide data to the control module 108. It is notable that the configuration of system 100 shown in FIG. 1 is merely an example, and variations to this design are contemplated herein. For instance, multiple UV light emitters (for example in the case where an appliance has multiple doors and therefore handles) and/or other sensors not shown in FIG. 1 may be employed. For instance, light sensors might be employed to detect when the room lights have been switched off which can serve as an indicator that the user has left the room, and thus the appliance handle is not in use and a cleaning cycle might be initiated. System 100 can be configured to include all commercially available sensors.

During operation, the UV light emitter 102 (located proximal to the door handle(s)—see below) automatically shines UV disinfecting light. Preferably, this occurs after each use of the door. Namely, it is desired that after the user opens and then closes the appliance door, the door's handle is disinfected via the UV light from the emitter 102.

A door sensor 106 serves as an indicator to control module 104 that the door has been closed. For example, door sensor 106 can be simple contact sensor or door opening sensor that detects when the appliance door is in a closed state. A contact sensor, for example, can detect when the door is in contact with its frame (as opposed to when the door is swung open and not in contact with the frame).

Control module 104 monitors the door state (i.e., open or closed), and once the door state changes, from open to closed, a cleaning cycle is initiated whereby the control module causes the UV light emitter 102 to shine UV disinfecting light on the door handle. In case a user decides to approach the door handle during a cleaning cycle, a proximity sensor 110 will alert the control module 104 (i.e., that the user's hand is in the proximity of the handle), which will immediately halt the cleaning cycle by deactivating the emitter 102 until the cleaning cycle is permitted to resume (e.g., once the user has moved away and the door has been closed). As will be described in detail below, revolving or retracting covers may be employed to shield the handle during a cleaning cycle. In that case, the proximity sensors 110 can also be used to indicate to the control module 104 when to retract the cover in response to a user approaching the handle.

Also, as will be described in detail below, the UV light is preferably propagated over the surface of the handle using a waveguide coating. A UV sensor/detector 108 can be coupled to the waveguide (e.g., opposite to the emitter) to detect how much, if any, UV light is escaping the waveguide. If a user were to grab the handle during a cleaning cycle, this can be detected via the UV detector and the cleaning cycle instantly halted.

Figure 2:
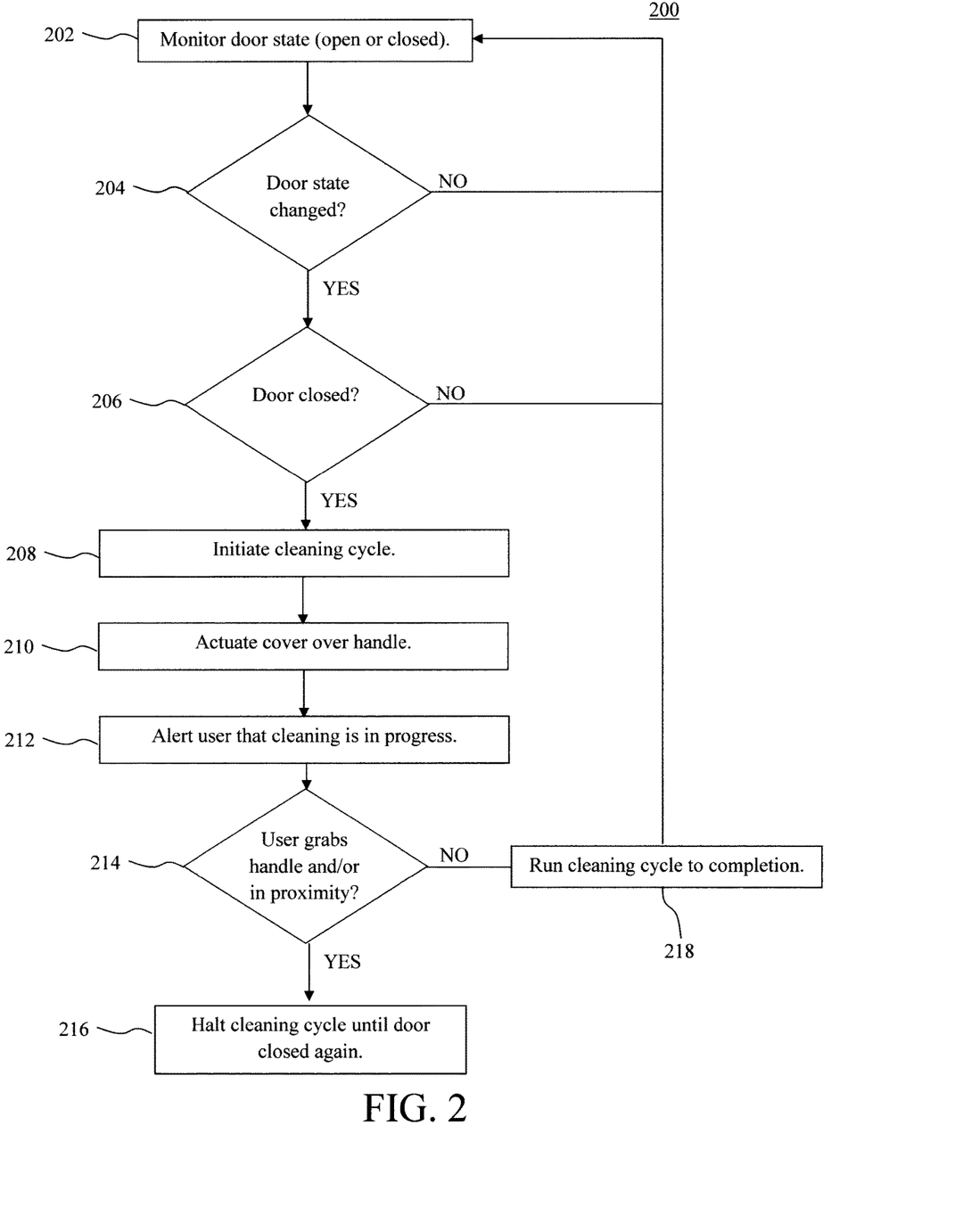
FIG. 2 is a diagram illustrating an exemplary methodology for automatically eradicating bio-related contaminants from appliance handles (e.g., using the system of FIG. 1) according to an embodiment of the present invention.

The general operation of system 100 is depicted in methodology 200 of FIG. 2. In step 202, the door state (i.e., open or closed) is monitored, e.g., via control module 108. When it is determined in step 204 that the door state has changed, and in step 206 that the door of the appliance is closed, e.g., via the door sensor 104, then in step 208 the control module initiates a cleaning cycle of the door handle, e.g., via UV disinfecting light from emitter 102. Otherwise, the control module continues to monitor the door state.

In step 210, a (e.g., revolving or sliding) cover can move over the handle for the duration of the cleaning cycle in order to prevent users from grabbing the handle. Various configurations of the cover are described in detail below. Additionally, in step 212 the user may be alerted that a cleaning cycle is in progress. For instance, a red light indicator can be turned on to indicate that disinfection is in progress. The red light indicator can be turned green once disinfection is completed.

As shown in FIG. 2, if it is determined during a cleaning cycle in step 214 that a user has grabbed the handle (e.g., via touch sensor 106) and/or is in proximity to the appliance (via a proximity sensor), then in step 216 the cleaning cycle is halted until the user has closed the door again (and has moved away from the appliance). Otherwise, the cleaning cycle is continued in step 218, e.g., for its given duration, and the control module continues to monitor the door state to detect the next time the door is opened/closed.

Given the above overview of the present techniques, some exemplary configurations for system 100 are now described. According to an exemplary embodiment, the UV disinfecting light from emitter 102 is propagated through a waveguide that wraps around the handle. For instance, the waveguide can be embodied as a coating on the handle. See FIG. 3.

Figure 3:
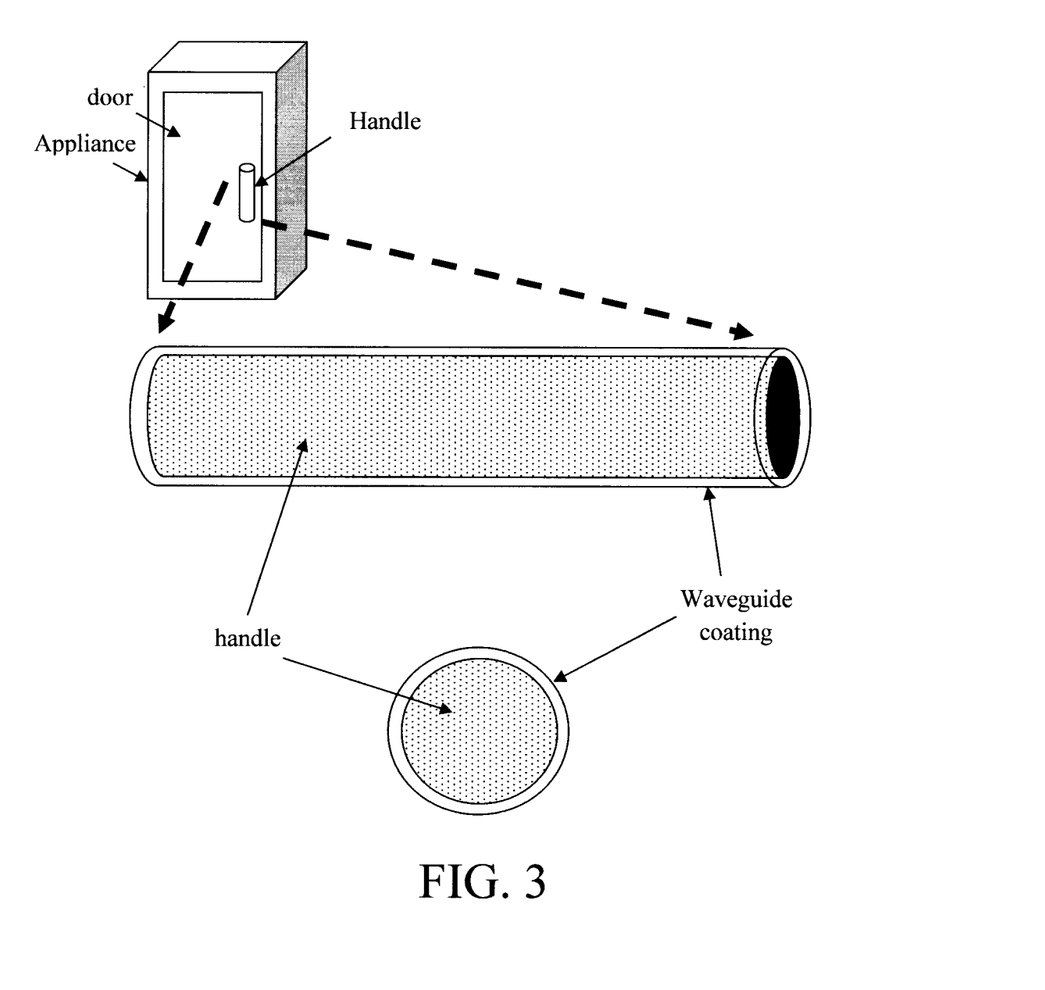
FIG. 3 is a diagram illustrating UV disinfecting light being propagated through a waveguide coating that wraps around the handle according to an embodiment of the present invention.

As shown in FIG. 3, the door handle is coated all-around with a layer that operates as a waveguide (labeled "Waveguide coating"). Suitable waveguide coatings include, but are not limited to, glass, polymer coatings (in particular polymers resistant to UV light), and some metal oxides with bandgap transparent to UV. For instance, a glass such as silicon dioxide $SiO_2$ is particularly well suited for the present process, as is a metal oxide such as aluminum oxide. The waveguide coating material needs to be resistant to UV light, and preferably also resistant to materials commonly used in cleaning appliances, such as detergents, disinfectants including those containing solvents such as alcohol, bleach, and chlorhexidine. By way of example only, the waveguide coating can be applied to the handle by dipping coating, spraying, etc. to a thickness of from about 1 micrometer ($\mu m$) to about 5 $\mu m$, and ranges therebetween. Thicker coatings can also be used. One may want to use a thicker coating, for instance, when the handle has surface roughness and a thicker, non-conformal coating would provide a smooth exterior surface for the handle.

In many applications (for example a fiber optics), the waveguide which contains the light is the core of the structure, and coatings may be applied to the waveguide core, e.g., for mechanical reasons. The waveguide does not, however, have to be the core per se, and in the present embodiments the core is the handle. All that is required is that the material outside of the waveguide will have a refractive index smaller than that of the waveguide material.

In the present case the material outside the waveguide is air n=1.0, while the waveguide is, e.g., glass with n=1.5 (or other suitable material—see above). The handle is typically made of metal which will reflect all the light back into the waveguide. The light is guided in the waveguide by a mechanism known as total internal reflections.

Advantageously, by forming a coating that wraps around the handle, the UV disinfecting light (which is propagated through the waveguide coating) will have access to all surfaces around the handle. This would not be the case if, for instance, one was to simply shine UV light onto the handle. Further, the present waveguide coating can be formed (e.g., by dipping, spraying, etc.—see above) on an ordinary appliance handle. Thus, the present techniques can be implemented in regular appliance manufacturing processes. The coating needs to wet the handle material to form a film. In cases where the material does not like to wet a surface, it is possible to overcome this by using an adhesion promoter. For instance, silanes can be used as adhesion promoters between $SiO_2$ and polymers such as polyimides.

Figure 4:
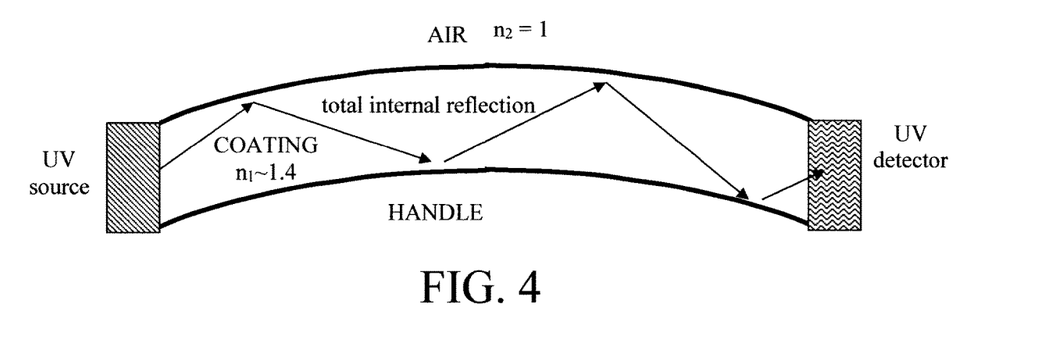
FIG. 4 is a schematic diagram illustrating UV disinfecting light being propagated through a waveguide coating from a UV source to a UV detector according to an embodiment of the present invention.
Figure 5:
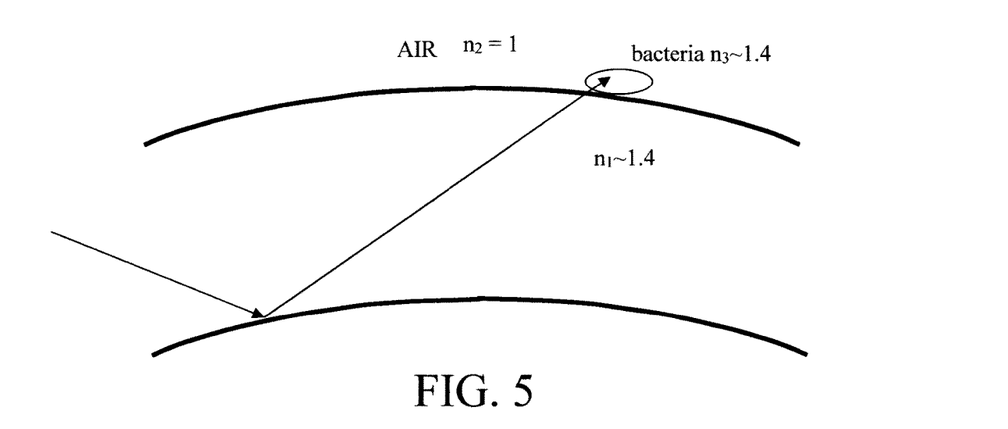
FIG. 5 is a schematic diagram illustrating localized leakage of UV disinfecting light at the site of a microorganism on the handle according to an embodiment of the present invention.

FIGS. 4 and 5 illustrate the principles behind the waveguide coating for use in propagating the UV disinfecting light. As shown in FIG. 4, a UV source is coupled to one (first) end of the waveguide coating. In this example, the UV source may be considered to be the UV light emitter 102 of the present system. According to an exemplary embodiment, the UV light source/emitter is an array of semiconductor light emitting diodes or LEDs, having as an active material gallium nitride (GaN), aluminum nitride (AlN), or alloys thereof such as indium-gallium-aluminum nitride ($In_xGa_{1-x}Al_yN_{1-y}$). The use of LEDs as a UV source has some notable advantages. For instance, the life time of LEDs can exceed 50 years so there is no maintenance (e.g., replacing a UV bulb). Also, LEDs are small and therefore can be easily embedded in tight spaces such at the base of the handle.

The UV light (from the UV source) that is coupled into the waveguide coating cannot escape the waveguide due to the large refractive index difference between the coating (e.g., a glass coating has a refractive index $n_1$ of about 1.5) and air (which has a refractive index $n_2$ of about 1. As a result, the UV light is internally reflected throughout the coating. See FIG. 4.

As shown in FIG. 4, a UV detector is coupled to a (second) end of the waveguide coating opposite the UV source. Thus, the waveguide coating propagates light from the UV source to the UV detector. The UV detector constantly monitors the UV power transmitted through the waveguide coating. When the UV detector detects a power drop, it suggests that UV light is leaking out of the waveguide coating. UV light leakage is expected when eradicating microorganisms on the surface of the waveguide coating/handle. See, for example, FIG. 5. When a microorganism, such as a bacteria, is present at the surface of the waveguide due to the large content of water in the bacteria UV light from the waveguide will leak into the bacteria (water has a high refractive index $n_3$ of about 1.4), thus effectively eradicating the bacteria. See for example FIG. 5 where it is shown that UV light leaks through the waveguide coating at the site of the bacteria. This happens locally, only where bacteria is present on the surface. Nucleic acids (RNA and DNA) are also vulnerable to UV radiation. Thus, other microorganisms such as viruses (which typically contain at least one of RNA and DNA), can be eradicated from the surface of the waveguide coating/handle. Further, viruses are often passed to surfaces (such as the handle in question) by a user touching the handle (which causes some humidity to pass from the user's hand to the handle), and/or the user speaking, coughing, sneezing, etc. (all which involve water-containing, e.g., aerosolized, droplets that land on the handle.

Based on the UV detector, a threshold can be preset such that if the level of UV light begin detected drops by more than the threshold amount (which indicates that too much UV light is leaking out of the waveguide) then the UV source is turned off, and the cleaning cycle is halted (see step 212 of methodology 200 of FIG. 2—above). By way of example only, if the amount of UV light detected drops by more than about 10%, then the UV source is shut off halting the cleaning cycle.

One reason the waveguide might become too "leaky" is if the handle becomes too dirty. For instance, an increased amount of bacteria on the handle increases the amount of UV light escaping from the waveguide coating, and thereby reduces the amount of UV light sensed by the detector. When the threshold is breached, the cleansing cycle will be halted, and the user alerted that the handle should be thoroughly cleaned by the user, e.g., wipe it with a cleaning cloth. Only when the amount of UV light reaching the detector is restored to acceptable levels (i.e., leaking is below the threshold) can the cleaning cycle commence again. Any type of visual and/or audible notification may be used to alert the user. For instance, a message could be provided on a display of the appliance, such as "Cleaning needed" or "Handle dirty, please wipe down." Similarly, these commands might be present on a control panel of the appliance and illuminated or otherwise highlighted to catch the user's attention.

Preferably, a cleaning cycle is run when no one is present. See, for example, the above-described warning light indicators that alert users that a cleaning cycle is being run, sensors to detect that no one is in the room, etc. To add an extra level of protection, the other various sensors and fail-safe mechanisms described above, such as touch and proximity sensors, can be used to halt the cleaning cycle in the event that a user, despite the warnings, approaches the handle. To provide yet another level of safety, an ultrafast "circuit breaker" safety feature can be employed. This feature is now described.

Another reason the waveguide coating might become too leaky is if the user, despite being alerted that cleaning is in progress (see step 212 of methodology 200 of FIG. 2), still grabs the handle. In that case, the UV light source is immediately and automatically turned off. The drop in the UV light can be detected on a time scale shorter than a microsecond, and shutting down the UV light source can also be done on the same time scale. As a result of this ultrafast "circuit breaker" safety feature, the exposure to UV light is minimal and is designed to be a small fraction of the exposure limits allowed by National Institute for Occupational Safety and Health (NIOSH). For additional safety, a proximity sensor can be used to shut down the UV source when a person's hand is approaching the door handle. It is notable, however, that only upon physical contact of the hand with the waveguide coating can UV light leak, since the UV light cannot escape the waveguide coating as long as it is surrounded by air.

Figures 6A, 6B:
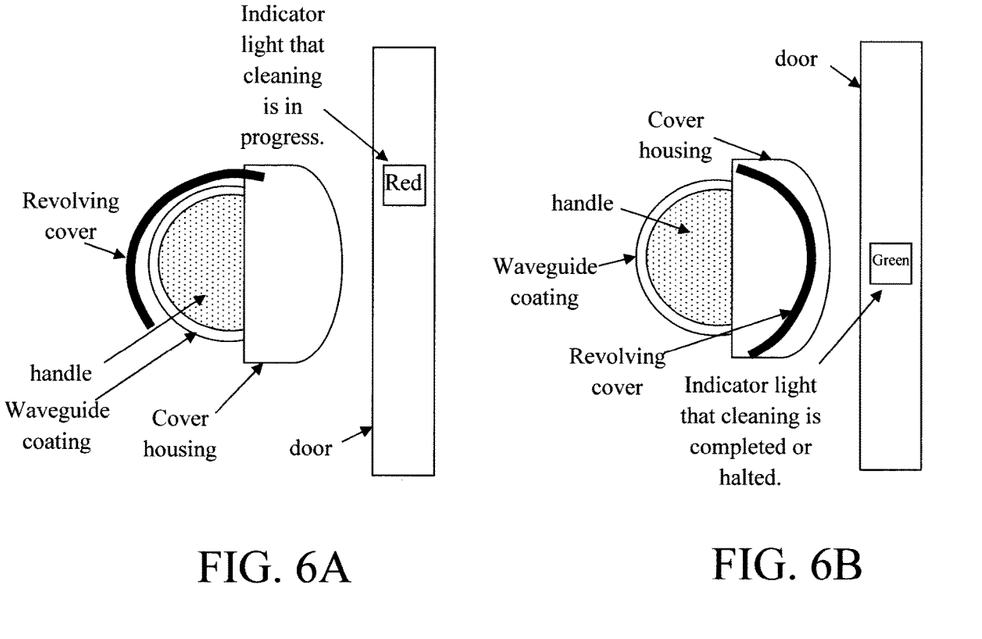
FIG. 6A is a side-view diagram illustrating a revolving cover being used to cover the handle during a cleaning cycle according to an embodiment of the present invention.
FIG. 6B is a side-view diagram illustrating the revolving cover having been retracted into its housing once the cleaning cycle has been completed (or has been halted) according to an embodiment of the present invention.

As described above, a cover can be employed that is actuated over the handle during a cleaning cycle. This will help prevent users from grabbing the handle while it is being cleaned via the above-described waveguide coating. In one exemplary embodiment, the cover revolves around the handle to cover the handle during a cleaning cycle and to expose the handle once cleaning is completed (or halted). See FIGS. 6A and 6B. Specifically, as shown in FIG. 6A, during a cleaning cycle, the cover (which can revolve in and out of a cover housing behind the handle) surrounds the handle. As described above, the cover can be engaged when the cleaning cycle is initiated (see step 210 of methodology 200 of FIG. 2). This will shield the handle during the cleaning cycle. Further, a red indicator light, or other form of alerting the user, may be turned on to indicate that a cleaning cycle is in progress.

As shown in FIG. 6B, when the cleaning cycle is completed (or halted), the cover retracts back into its housing, exposing the handle which can then be gripped by the user to open the door. The indicator light changes to green letting the user know it is okay to use the handle. Naturally, the revolving cover may retract when the cleaning cycle has run to completion (see step 218 of methodology 200 of FIG. 2). However, as described above, the cleaning cycle might also be halted if the user decides to grab the handle during the cleaning cycle. According to an exemplary embodiment, proximity sensors (see above) are employed that detect the user is approaching the handle, the cleaning cycle is immediately halted, and the cover is retracted into its housing. Only when (via the proximity sensors) it is determined that the user has moved away from the appliance, will the cover rotate back over the handle, and the cleaning cycle recommence until completion.

Figure 7:
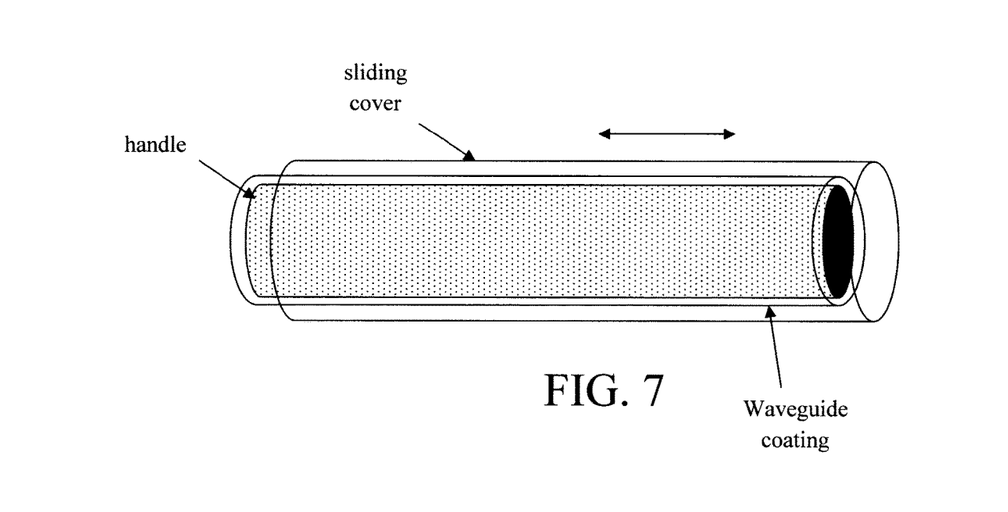
FIG. 7 is a diagram illustrating a sliding cover which can be used to cover the handle during a cleaning cycle according to an embodiment of the present invention.

Another configuration anticipated herein for the cover mechanism is shown in FIG. 7. In this example, the cover is a sliding (as opposed to rotating) cover. Namely, as shown in FIG. 7, this cover, when actuated (e.g., during a cleaning cycle) slides over and covering the handle. When the cleaning cycle is complete (or halted), the cover can retract by sliding to expose the handle, which can then be used to open the door. Namely, in the same manner as described above with respect to the revolving cover, proximity sensors can be employed to determine when a user is approaching the handle, at which time the cleaning cycle can be halted and the cover retracted to permit the user to grab the handle. Only when it is determined that the user has moved away from the appliance, will the cover slide back over the handle, and the cleaning cycle recommence until completion.

Figure 8:
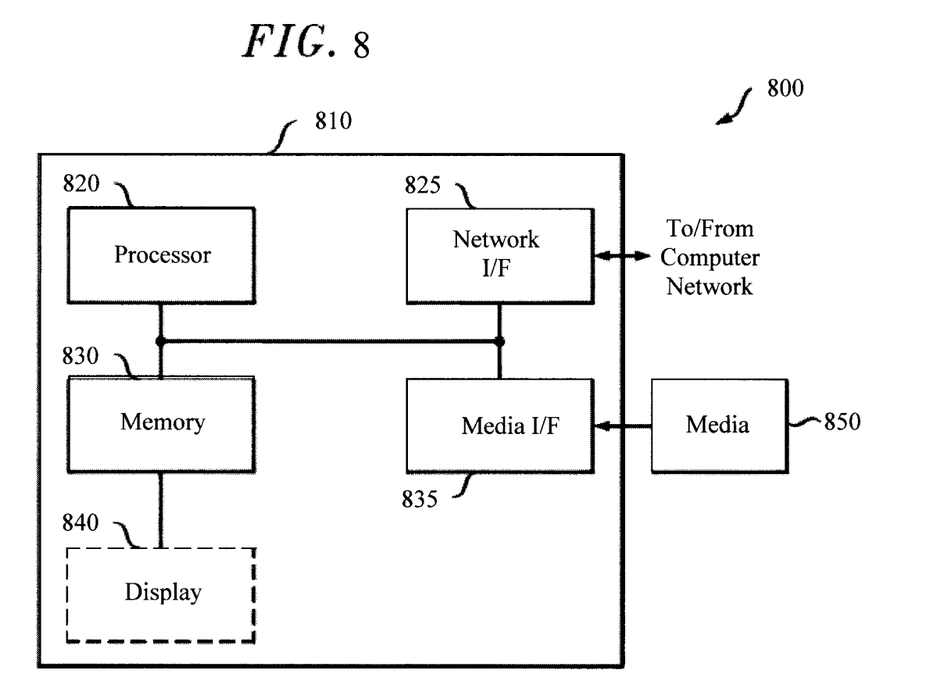
FIG. 8 is a diagram illustrating an exemplary apparatus for performing one or more of the methodologies presented herein according to an embodiment of the present invention.

Turning now to FIG. 8, a block diagram is shown of an apparatus 800 for implementing one or more of the methodologies presented herein. By way of example only, apparatus 800 is representative of the control module 104 (of system 100 of FIG. 1) and can be configured to implement one or more of the steps of methodology 200 of FIG. 2.

Apparatus 800 includes a computer system 810 and removable media 850. Computer system 810 includes a processor device 820, a network interface 825, a memory 830, a media interface 835 and an optional display 840. Network interface 825 allows computer system 810 to connect to a network, while media interface 835 allows computer system 810 to interact with media, such as a hard drive or removable media 850.

Processor device 820 can be configured to implement the methods, steps, and functions disclosed herein. The memory 830 could be distributed or local and the processor device 820 could be distributed or singular. The memory 830 could be implemented as an electrical, magnetic or optical memory, or any combination of these or other types of storage devices. Moreover, the term "memory" should be construed broadly enough to encompass any information able to be read from, or written to, an address in the addressable space accessed by processor device 820. With this definition, information on a network, accessible through network interface 825, is still within memory 830 because the processor device 820 can retrieve the information from the network. It should be noted that each distributed processor that makes up processor device 820 generally contains its own addressable memory space. It should also be noted that some or all of computer system 810 can be incorporated into an application-specific or general-use integrated circuit.

Optional display 840 is any type of display suitable for interacting with a human user of apparatus 800. Generally, display 840 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A system for eradicating biological contaminants from a handle on an appliance door, the system comprising:
   an ultraviolet (UV) light emitter for producing UV disinfecting light during a cleaning cycle;
   a waveguide coating that fully wraps around the handle, coupled to the UV light emitter, for propagating the UV disinfecting light over a surface of the handle;
   a UV detector that detects the UV disinfecting light being transmitted through the waveguide coating; and
   a control module comprising a processor, connected to a memory, configured to: obtain data from the UV detector, halt the cleaning cycle when the UV disinfecting light being transmitted through the waveguide coating drops by more than a preset threshold amount indicating that the handle is too dirty, and alert a user that the handle should be cleaned by the user.

2. The system of claim 1, further comprising:
   at least one sensor for indicating to the control module as to when to initiate or halt the cleaning cycle.

3. The system of claim 2, wherein the at least one sensor comprises a door sensor for determining a state of the appliance door as either opened or closed.

4. The system of claim 3, wherein the door sensor comprises a contact sensor for detecting when the appliance door is in contact with a frame of the appliance door.

5. The system of claim 2, wherein the at least one sensor comprises a proximity sensor for determining when a user is approaching the handle.

6. The system of claim 1, wherein the UV detector is coupled to an end of the waveguide coating opposite the UV light emitter.

7. The system of claim 1, further comprising:
   a cover for shielding the handle during the cleaning cycle.

8. The system of claim 7, wherein the cover is a revolving cover.

9. The system of claim 8, further comprising:
   a cover housing behind the handle.

10. The system of claim 7, wherein the cover is a sliding cover.

11. The system of claim 1, wherein the waveguide coating is formed from a material selected from the group consisting of: glass, polymer coatings, metal oxides, and combinations thereof.

12. The system of claim 1, wherein the waveguide coating is formed from aluminum oxide.

13. The system of claim 1, wherein the waveguide coating has a thickness of from about 1 micrometer ($\mu$m) to about 5 $\mu$m, and ranges therebetween.

14. The system of claim 1, wherein the handle is made of metal.

15. The system of claim 1, wherein the UV light emitter comprises an array of semiconductor light emitting diodes.

16. A system for eradicating biological contaminants from a handle on an appliance door, the system comprising:
- a UV light emitter for producing UV disinfecting light during a cleaning cycle;
- a waveguide coating that fully wraps around the handle, coupled to the UV light emitter, for propagating the UV disinfecting light over a surface of the handle;
- a UV detector that detects the UV disinfecting light being transmitted through the waveguide coating;
- a control module for controlling the UV light emitter; and
- at least one sensor for indicating to the control module as to when to initiate or halt the cleaning cycle, wherein the at least one sensor comprises a light sensor for detecting when lights have been switched off in a room with the appliance and that the cleaning cycle can be initiated,
- wherein the control module comprises a processor, connected to a memory, configured to: obtain data from the UV detector, halt the cleaning cycle when the UV disinfecting light being transmitted through the waveguide coating drops by more than a preset threshold amount indicating that the handle is too dirty, and alert a user that the handle should be cleaned by the user.

17. The system of claim 16, wherein the UV detector is coupled to an end of the waveguide coating opposite the UV light emitter.

18. The system of claim 16, wherein the waveguide coating is formed from a material selected from the group consisting of: glass, polymer coatings, metal oxides, and combinations thereof.

* * * * *